US009140538B2

(12) United States Patent
Hirota

(10) Patent No.: US 9,140,538 B2
(45) Date of Patent: Sep. 22, 2015

(54) OPTICAL TOMOGRAPHIC IMAGING SYSTEM AND OPTICAL TOMOGRAPHIC IMAGING METHOD TO GENERATE TOMOGRAPHIC IMAGE AND SURFACE IMAGE OF A SUBJECT

(75) Inventor: Kazuhiro Hirota, Kanagawa (JP)

(73) Assignee: TOPCON CORPORATION, Tokyo (JP)

( * ) Notice: Subject to any disclaimer, the term of this patent is extended or adjusted under 35 U.S.C. 154(b) by 305 days.

(21) Appl. No.: 13/813,380

(22) PCT Filed: Jul. 27, 2011

(86) PCT No.: PCT/JP2011/067060
§ 371 (c)(1),
(2), (4) Date: Apr. 3, 2013

(87) PCT Pub. No.: WO2012/014920
PCT Pub. Date: Feb. 2, 2012

(65) Prior Publication Data

US 2013/0182261 A1 Jul. 18, 2013

(30) Foreign Application Priority Data

Jul. 30, 2010 (JP) ................................ 2010-172682

(51) Int. Cl.
*G01B 11/02* (2006.01)
*G01B 9/02* (2006.01)
(Continued)

(52) U.S. Cl.
CPC ........ *G01B 9/02091* (2013.01); *A61B 1/00167* (2013.01); *A61B 1/00172* (2013.01); *A61B 5/0066* (2013.01); *A61B 5/6852* (2013.01); *G01N 21/4795* (2013.01)

(58) Field of Classification Search
CPC ............. G01B 9/02091; A61B 5/0066; A61B 5/0073; A61B 3/102; A61B 1/00167; A61B 1/00172; A61B 5/6852; G01N 21/4795; G01N 2021/1787
USPC .................................................. 356/479, 497
See application file for complete search history.

(56) References Cited

U.S. PATENT DOCUMENTS

2006/0077395 A1 4/2006 Chan et al.
2006/0119858 A1 * 6/2006 Knighton et al. ............. 356/479
(Continued)

FOREIGN PATENT DOCUMENTS

JP 2005083929 A 3/2005
JP 2006112864 A 4/2006
(Continued)

OTHER PUBLICATIONS

Jioa, Shuliang, Simultaneous acquisition of sectional and fundus ophthalmic images with spectral-domain optical coherence tomography, Jan. 24, 2005, Optic Express, vol. 13, No. 2, pp. 444-452.*

(Continued)

*Primary Examiner* — Tarifur Chowdhury
*Assistant Examiner* — Michael P Lapage
(74) *Attorney, Agent, or Firm* — Pearne & Gordon LLP

(57) ABSTRACT

An optical tomographic imaging method according to one aspect of the present invention is a method of: splitting light emitted from a wavelength sweep light source into measuring light and reference light; radiating the measuring light onto a measuring subject; combining reflection light from the measuring subject with the reference light; detecting interfered light obtained by combining the reflection light with the reference light as an interference signal; and Fourier-transforming the interference signal to acquire a tomographic image of the measuring subject, and includes steps of: generating tomographic data of the measuring subject based on the interference signal; generating surface data of the measuring subject based on the interference signal; constructing a tomographic image that is based on the generated tomographic data; constructing a surface image that is based on the outputted surface data; and generating a display image from the tomographic image and the surface image.

10 Claims, 11 Drawing Sheets

(51) Int. Cl.

| | |
|---|---|
| ***A61B 1/00*** | (2006.01) |
| ***A61B 5/00*** | (2006.01) |
| ***G01N 21/47*** | (2006.01) |

(56) References Cited

U.S. PATENT DOCUMENTS

| | | | | |
|---|---|---|---|---|
| 2007/0159596 | A1 | 7/2007 | Fukuma et al. | |
| 2008/0151187 | A1* | 6/2008 | Tsukada et al. | 351/206 |
| 2010/0041948 | A1 | 2/2010 | Watanabe | |
| 2010/0069747 | A1 | 3/2010 | Watanabe et al. | |
| 2010/0110172 | A1 | 5/2010 | Satake | |
| 2010/0165289 | A1 | 7/2010 | Nozato et al. | |
| 2012/0063660 | A1* | 3/2012 | Imamura et al. | 382/131 |
| 2012/0092617 | A1* | 4/2012 | Muto et al. | 351/206 |

FOREIGN PATENT DOCUMENTS

| | | | |
|---|---|---|---|
| JP | 2007185243 | A | 7/2007 |
| JP | 2010-043994 | A | 2/2010 |
| JP | 2010-068865 | A | 4/2010 |
| JP | 2010-110393 | A | 5/2010 |
| JP | 2010158265 | A | 7/2010 |
| JP | 2010158343 | A | 7/2010 |
| WO | 2010/067813 | A1 | 6/2010 |
| WO | 2010079550 | A1 | 7/2010 |

OTHER PUBLICATIONS

European Search Report for Application No. EP 11 81 2509 dated Nov. 29, 2013.

European Search Report for Application No. EP 11 81 2509.5 dated Dec. 9, 2013.

Translation of the International Search Report on Patentability for PCT/JP2011/067060 dated Feb. 14, 2013.

Japanese Office action for 2010-172682 dated Jul. 8, 2014.

International Search Report for PCT/JP2011/067060 dated Nov. 8, 2011.

Jiao, Shuliang et, al. "Simultaneous acquisition of sectional and fundus opthalmic images with spectral-domain optical coherence tomography" IN: Optics Express Jan. 24, 2005, vol. 13, No. 2 pp. 444-452.

European Office action for 11812505.5-1657 dated Jun. 18, 2015.

* cited by examiner

OPTICAL TOMOGRAPHIC IMAGING SYSTEM AND OPTICAL TOMOGRAPHIC IMAGING METHOD TO GENERATE TOMOGRAPHIC IMAGE AND SURFACE IMAGE OF A SUBJECT

TECHNICAL FIELD

The present invention relates to an optical tomographic imaging system and an optical tomographic imaging method, and in particular, to an optical tomographic imaging system and an optical tomographic imaging method that allow a tomographic image and a surface image to be created in real time and at the same time.

BACKGROUND ART

Currently, there is a need to acquire a detailed tomogram of a living body for the purpose of making a diagnosis of cancer or the like. As a method for acquiring a detailed tomogram of a living body, "Time domain OCT" has been proposed from the past, in which a tomographic image of a subject is obtained by scanning with light outputted from a low coherence light source.

Further, in recent years, Frequency domain OCT has been used, which is improved OCT that has solved such problems that an optimal signal/noise ratio (S/N ratio) cannot be obtained, an image capturing frame rate is low, and a penetration depth (an observation depth) is small, which are disadvantages of "Time domain OCT."

As representative apparatus configurations to carry out Frequency domain OCT measurement, an SD-OCT (Spectral Domain OCT) apparatus and SS-OCT (Swept Source OCT) of two types can be cited.

The SD-OCT apparatus uses broad bandwidth low coherence light such as an SLD (Super Luminescence Diode), an ASE (Amplified Spontaneous Emission) light source, and white light as a light source and splits the broad bandwidth low coherence light into measuring light and reference light using a Michelson type interferometer or the like. Thereafter, the SD-OCT apparatus radiates the measuring light onto a measuring subject, causes reflection light that has been reflected by the measuring subject and has returned and the reference light to interfere with each other, and splits this interfered light into respective frequency components using a spectrometer. Then, the SD-OCT apparatus measures an interfered light intensity for each frequency component using a detector array in which elements such as photodiodes are arranged in an array. The SD-OCT apparatus Fourier-transforms a spectral interference intensity signal that has been obtained by measuring the interfered light intensity with a computer, to thereby compose a tomographic image.

On the other hand, the SS-OCT apparatus uses as a light source a laser that temporally sweeps an optical frequency and causes the reflection light and the reference light to interfere with each other at respective wavelengths. The SS-OCT apparatus measures a temporal waveform of a signal that corresponds to a temporal change in the optical frequency. Then, the SS-OCT apparatus Fourier-transforms a spectral interference intensity signal that has been obtained through the measurement of the temporal waveform with a computer, to thereby compose a tomographic image.

Now, in a diagnosis of cancer through an endoscope, it is typical in recent years that an extent of progression of cancer is determined from a surface condition of a lesion observed through the endoscope.

Thus, in an OCT apparatus (an optical tomographic imaging system) as well, it is extremely effective if not only a conventional tomographic image but also a surface condition of a lesion can be observed at the same time. With such a demand, a technique is disclosed in which a tomogram in a direction parallel to a surface is generated from three dimensional volume data after all tomographic images are acquired and is used in a diagnosis of cancer (see PTL 1).

CITATION LIST

Patent Literature

{PTL 1}: Japanese Patent Application Laid-Open No. 2010-068865

SUMMARY OF INVENTION

Technical Problem

However, with the technique disclosed in PTL 1, there is a problem in that the surface condition cannot be observed in real time since the tomogram in the direction parallel to the surface is re-composed from the three dimensional volume data and is displayed after all the tomographic images are acquired. Further, there is a problem in that the re-composed image cannot be constructed unless all the tomographic images have been acquired.

The present invention has been made in view of such issues, and it is an object to provide an optical tomographic imaging system and an optical tomographic imaging method that allows a tomographic image and a surface image to be created in real time and at the same time.

Solution to Problem

In order to achieve the aforementioned object, an optical tomographic imaging system according to one aspect of the present invention is an optical tomographic imaging system configured to split light emitted from a wavelength sweep light source into measuring light and reference light, configured to radiate the measuring light onto a measuring subject, configured to combine reflection light from the measuring subject with the reference light, configured to detect interfered light that is obtained by combining the reflection light with the reference light as an interference signal, and configured to Fourier-transform the interference signal to acquire a tomographic image of the measuring subject, and the optical tomographic imaging system includes: a tomographic data generating unit configured to generate tomographic data of the measuring subject based on the interference signal; a surface data generating unit configured to carry out processing in parallel with the tomographic data generating unit and configured to generate surface data of the measuring subject based on the interference signal; a tomographic image constructing unit configured to construct a tomographic image that is based on the tomographic data generated by the tomographic data generating unit; a surface image constructing unit configured to construct a surface image that is based on the surface data generated by the surface data generating unit; and a display image generating unit configured to generate a display image from the tomographic image and the surface image.

According to the optical tomographic imaging system of the above aspect, generation of the tomographic data and generation of the surface data are carried out in parallel, and thus the tomographic image and the surface image can be created in real time and at the same time. This makes it possible for an operator to observe not only a tomographic image of a lesion portion but also a surface image at the same time, which facilitates a selection of a method of treatment.

In the optical tomographic imaging system of the above aspect, it is preferable that the surface data generating unit includes an absolute value converting unit configured to output absolute value data in which an amplitude value of the interference signal is converted into an absolute value; and an interference waveform data integrating unit configured to entirely integrate the absolute value data in a temporal direction.

In the optical tomographic imaging system of the above aspect, it is preferable that the surface data generating unit further includes a logarithmic transformation unit configured to logarithmically transform data that have been entirely integrated by the interference waveform data integrating unit.

In the optical tomographic imaging system of the above aspect, it is preferable that the surface data generating unit further includes a high pass filter configured to remove a low frequency component from the interference signal, and that the surface data generating unit inputs an interference signal from which a low frequency component has been removed by the high pass filter to the absolute value converting unit.

In the optical tomographic imaging system of the above aspect, it is preferable that a frame thinning unit configured to carry out thinning processing on the interference signal on a frame-by-frame basis is further provided and that an interference signal subjected to the thinning processing by the frame thinning unit is inputted to the tomographic data generating unit.

In the optical tomographic imaging system of the above aspect, it is preferable that the surface data generating unit includes a Fourier transformation unit configured to Fourier transform the interference signal to output Fourier transformation data; and a Fourier transformation data integrating unit configured to entirely integrate the Fourier transformation data in a frequency axis direction.

In the optical tomographic imaging system of the above aspect, it is preferable that the surface data generating unit further includes a logarithmic transformation unit configured to logarithmically transform data that have been entirely integrated by the Fourier transformation data integrating unit.

In the optical tomographic imaging system of the above aspect, it is preferable that the surface data generating unit further includes a high pass filter configured to remove a low frequency component from the Fourier transformation data, and that the surface data generating unit inputs Fourier transformation data from which a low frequency component has been removed by the high pass filter to the Fourier transformation data integrating unit.

In the optical tomographic imaging system of the above aspect, it is preferable that the display image generating unit generates an image in which the tomographic image and the surface image are arranged side by side.

Further, in order to achieve the aforementioned object, an optical tomographic imaging method according to one aspect of the present invention is an optical tomographic imaging method of: splitting light emitted from a wavelength sweep light source into measuring light and reference light; radiating the measuring light onto a measuring subject; combining reflection light from the measuring subject with the reference light; detecting interfered light obtained by combining the reflection light with the reference light as an interference signal; and Fourier-transforming the interference signal to acquire a tomographic image of the measuring subject, and the optical tomographic imaging method includes: a tomographic data generating step of generating tomographic data of the measuring subject based on the interference signal; a surface data generating step of carrying out processing in parallel with the tomographic data generating step and generating surface data of the measuring subject based on the interference signal; a tomographic image constructing step of constructing a tomographic image that is based on the tomographic data generated in the tomographic data generating step; a surface image constructing step of constructing a surface image that is based on the surface data outputted in the surface data generating step; and a display image generating step of generating a display image from the tomographic image and the surface image.

According to the optical tomographic imaging method of the above aspect, generation of the tomographic data and generation of the surface data are carried out in parallel, and thus the tomographic image and the surface image can be created in real time and at the same time. This makes it possible for an operator to observe not only a tomographic image of a lesion portion but also a surface image at the same time, which facilitates a selection of a method of treatment.

In the optical tomographic imaging method of the above aspect, it is preferable that the surface data generating step includes: an absolute value converting step of outputting absolute value data in which an amplitude value of the interference signal is converted into an absolute value; and an interference waveform data integrating step of entirely integrating the absolute value data in a temporal direction.

In the optical tomographic imaging method of the above aspect, it is preferable that the surface data generating step further includes a logarithmic transformation step of logarithmically transforming data that have been entirely integrated in the interference waveform data integrating step.

In the optical tomographic imaging method of the above aspect, it is preferable that the surface data generating step includes a step of removing a low frequency component from the interference signal with a high pass filter and that an interference signal from which a low frequency component has been removed in the step is used in the absolute value converting step.

In the optical tomographic imaging method of the above aspect, it is preferable that a frame thinning step of carrying out thinning processing on the interference signal on a frame-by-frame basis is further included and that an interference signal subjected to thinning processing in the frame thinning step is used in the tomographic data generating step.

In the optical tomographic imaging method of the above aspect, it is preferable that the surface data generating step includes a Fourier transformation step of Fourier-transforming the interference signal to output Fourier transformation data and an Fourier transformation data integrating step of entirely integrating the Fourier transformation data in a frequency axis direction.

In the optical tomographic imaging method of the above aspect, it is preferable that the surface data generating step further includes a logarithmic transformation step of logarithmically transforming data that have been entirely integrated in a frequency axis direction in the Fourier transformation data integrating step.

In the optical tomographic imaging method of the above aspect, it is preferable that the surface data generating step includes a step of removing a low frequency component from the Fourier transformation data with a high pass filter and that Fourier transformation data from which a low frequency component has been removed in the step are used in the Fourier transformation data integrating step.

In the optical tomographic imaging method of the above aspect, it is preferable that in the display image generating step, an image in which the tomographic image and the surface image are arranged side by side are generated.

Advantageous Effects of Invention

According to the present invention, generation of the tomographic data and generation of the surface data are carried out in parallel, and thus the tomographic image and the surface image can be created in real time and at the same time. This makes it possible for an operator to observe not only a tomographic image of a lesion portion but also a surface image at the same time, which facilitates a selection of a method of treatment.

DESCRIPTION OF EMBODIMENTS

Hereinafter, preferred embodiments of the present invention will be described in detail along with the accompanying drawings.

[First Embodiment]

First, a first embodiment of the present invention will be described.

<External View of Diagnostic Imaging Apparatus>

Figure 1:
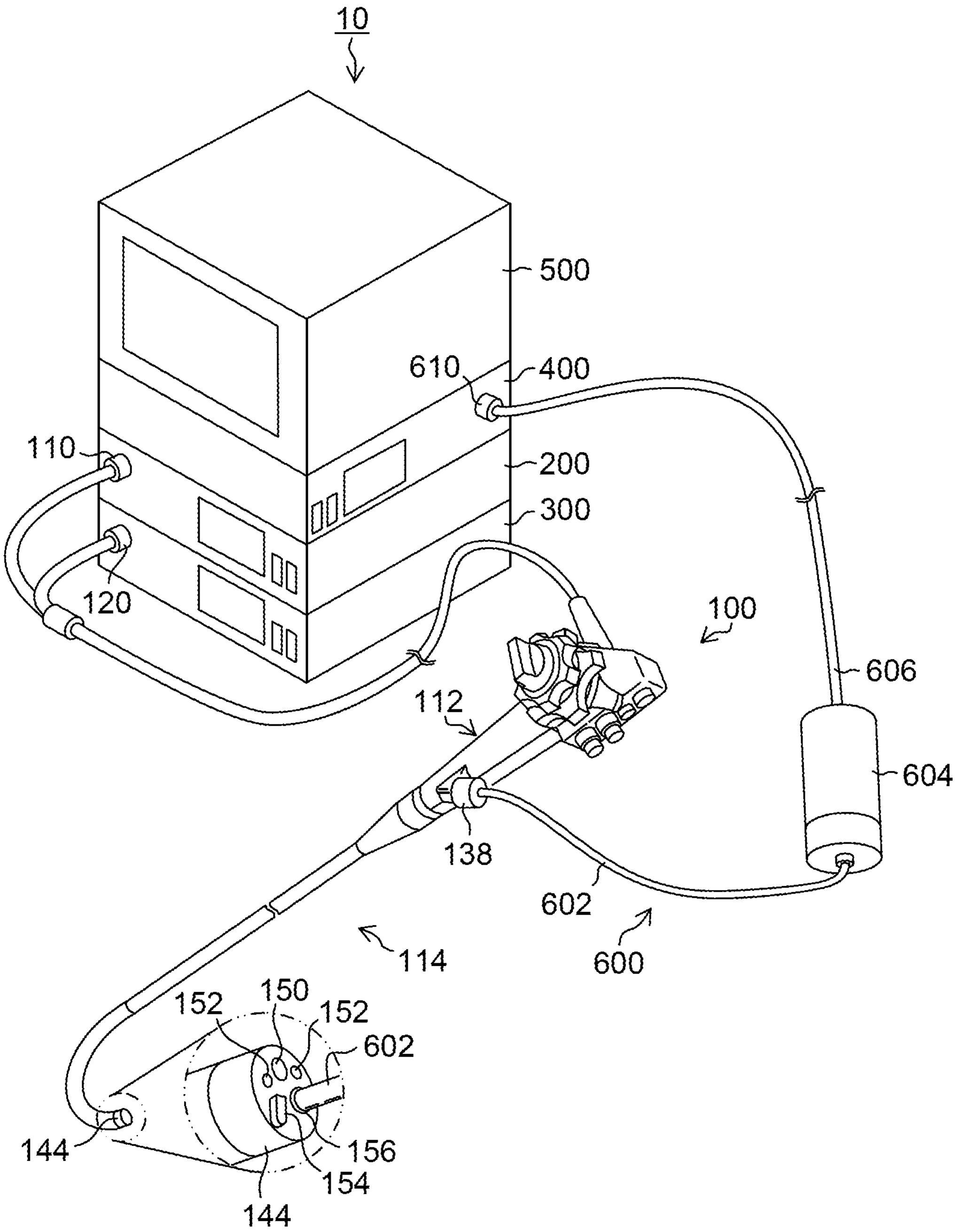
FIG. 1 is an external view that illustrates a diagnostic imaging apparatus where an optical tomographic imaging system according to a first embodiment is used.

FIG. 1 is an external view that illustrates a diagnostic imaging apparatus where an optical tomographic imaging system according to the first embodiment of the present invention is used.

As illustrated in FIG. 1, a diagnostic imaging apparatus 10 includes an endoscope 100, an endoscope processor 200, a light source device 300, an optical tomographic imaging system (for example, an OCT processor) 400, and a monitor device 500. Note that the endoscope processor 200 may be configured to have the light source device 300 integrated therein.

The endoscope 100 includes a hand operating unit 112 and an insertion unit 114 that is provided consecutively from this hand operating unit 112. An operator grips the hand operating unit 112 to operate it and inserts the insertion unit 114 into a body of a subject, to thereby observe the interior of the body of the subject.

The hand operating unit 112 is provided with a forceps insertion unit 138, and this forceps insertion unit 138 is in communication with a forceps opening 156 at a leading end portion 144. In the present embodiment, an OCT probe 600 is inserted into the forceps insertion unit 138, and thus the OCT probe 600 is led out from the forceps opening 156. The OCT probe 600 includes an insertion unit 602 that is inserted into the forceps insertion unit 138 and led out from the forceps opening 156, an operating unit 604 for the operator to operate the OCT probe 600, and a cable 606 that is connected to the OCT processor 400 through a connector 610.

<Configurations of Endoscope, Endoscope Processor, and Light Source Device>

[Endoscope]

An observation optical system 150, an illumination optical system 152, and a CCD (charge-coupled device, not illustrated) are provided at the leading end portion 144 of the endoscope 100.

The observation optical system 150 forms an image of the subject on a light receiving surface of the CCD, which is not illustrated. The CCD converts the image of the subject that has been formed on the light receiving surface thereof into an electrical signal through each light receiving element. The CCD of the present embodiment is a CCD in which color filters of three primary colors of red (R), green (G), and blue (B) are arranged in a predetermine arrangement (Bayer arrangement or honeycomb arrangement) for each pixel.

Note that the reference numeral 154 designates a cleaning nozzle for supplying at least one of cleaning liquid and pressurized air toward the observation optical system 150.

[Light Source Device]

The light source device 300 causes visible light to enter a light guide, which is not illustrated. One end of the light guide is connected to the light source device 300 through an LG connector 120, and the other end of the light guide faces the illumination optical system 152. Light that is emitted from the light source device 300 is emitted from the illumination optical system 152 via the light guide and illuminates a field of view range of the observation optical system 150.

[Endoscope Processor]

An image signal outputted from the CCD is inputted to the endoscope processor 200 through an electrical connector 110. An analog image signal outputted from the CCD is converted into a digital image signal in the endoscope processor 200 and subjected to processing necessary to be displayed on a screen of the monitor device 500.

In this way, observation image data that have been obtained by the endoscope 100 are outputted to the endoscope processor 200, and an image is displayed on the monitor device 500 that is connected to the endoscope processor 200.

<Internal Configurations of OCT Processor and OCT Probe>

Figure 2:
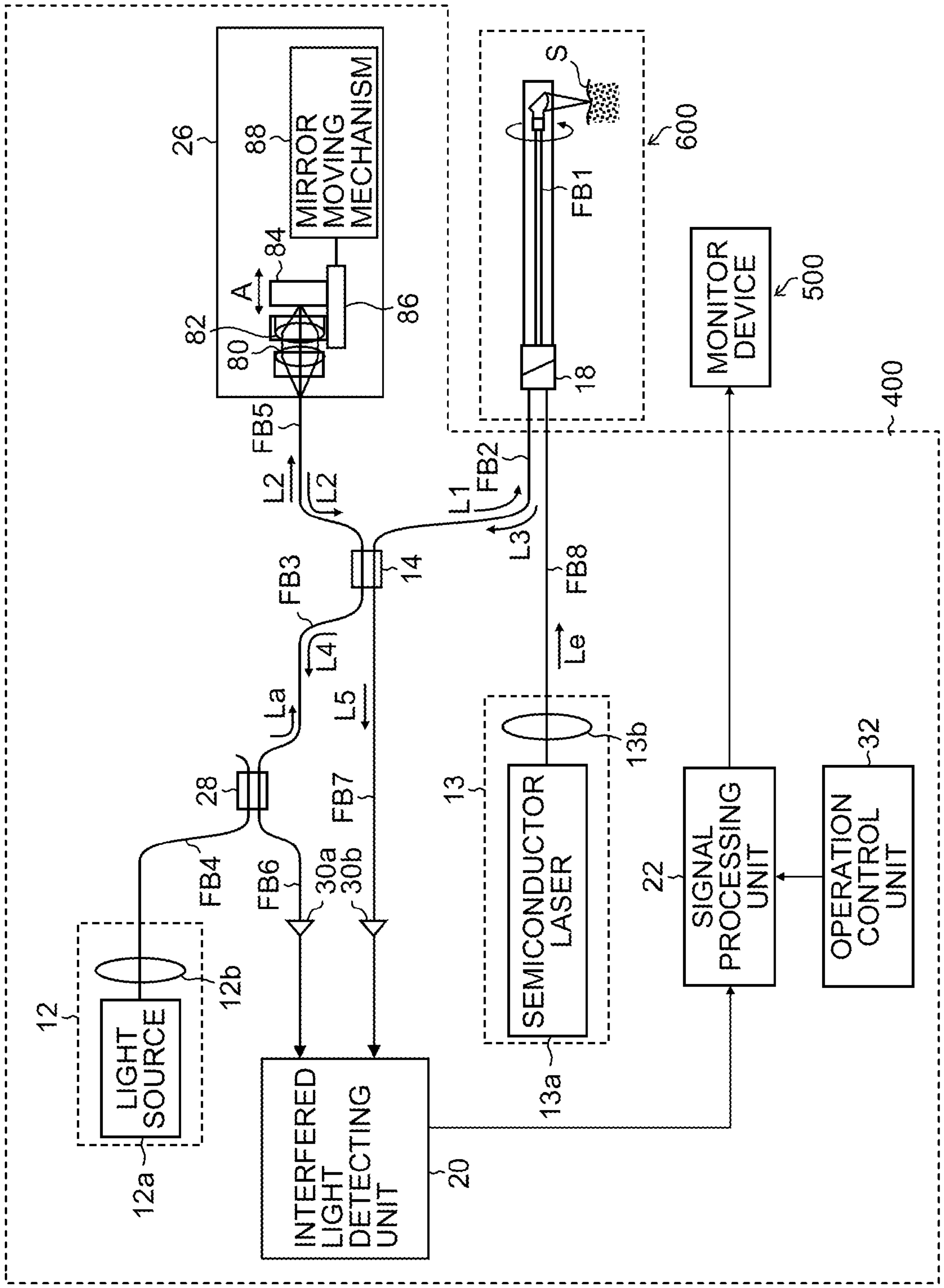
FIG. 2 is a block diagram that illustrates an internal configuration of an OCT processor of FIG. 1.

FIG. 2 is a block diagram that illustrates an internal configuration of the OCT processor of FIG. 1.

[OCT Processor]

The OCT processor 400 and the OCT probe 600 illustrated in FIG. 2 are for acquiring an optical tomographic image of a measuring subject through an optical coherence tomography (OCT) measuring method and include a first light source unit (a first light source unit) 12 that emits light La for measurement, an optical fiber coupler (a splitting and combining unit) 14 that splits the light La emitted from the first light source unit 12 into measuring light (a first light beam) L1 and reference light L2 and also combines returning light L3 from a measuring subject S serving as the subject with the reference light L2 to generate interfered lights L4 and L5, the OCT probe 600 that includes a rotative side optical fiber FB1 that guides the measuring light L1 split by the optical fiber coupler 14 to the measuring subject and also guides the returning light L3 from the measuring subject, a fixed side optical fiber FB2 that guides the measuring light L1 to the rotative side optical fiber FB1 and also guides the returning light L3 guided by the rotative side optical fiber FB1, an optical connector 18 that rotatably connects the rotative side optical fiber FB1 to the fixed side optical fiber FB2 and transmits the measuring light L1 and the returning light L3, an interfered light detecting unit 20 that detects the interfered lights L4 and L5 generated by the optical fiber coupler 14 as an interference signal, and a signal processing unit 22 that processes the interference signal detected by this interfered light detecting unit 20 to acquire an optical tomographic image (hereinafter, simply referred to as a "tomographic image" as well). Further, the optical tomographic image that has been acquired by the signal processing unit 22 is displayed on the monitor device 500.

Further, the OCT processor 400 includes a second light source unit (a second light source unit) 13 that emits aiming light (a second light beam) Le for indicating a mark for measurement, an optical path length adjusting unit 26 that adjusts an optical path length of the reference light L2, an optical fiber coupler 28 that disperses the light La emitted from the first light source unit 12, detectors 30*a* and 30*b* that detect the interfered lights L4 and L5 that have been combined in the optical fiber coupler 14, and an operation control unit 32 that carries out input of various conditions, modifications of settings, and so on in the signal processing unit 22.

Note that, in the OCT processor 400 illustrated in FIG. 2, various optical fibers FB (FB3, FB4, FB5, FB6, FB7, FB8, and so on) including the rotative side optical fiber FB1 and the fixed side optical fiber FB2 are used as optical paths for guiding and transmitting various lights including the aforementioned emitted light La, the aiming light Le, the measuring light L1, the reference light L2, the returning light L3, and so on among constituent elements such as respective optical devices.

The first light source unit 12 emits light (for example, laser light or low coherence light at a wavelength of 1.3 μm) for the OCT measurement. This first light source unit 12 is a light source that emits the laser light La that is centered in an infrared region (for example, at a wavelength of 1.3 μm) while sweeping a frequency at a constant cycle. This first light source unit 12 includes a light source 12*a* that emits the laser light or low coherence light La and a lens 12*b* that converges the light La emitted from the light source 12*a*. Further, although details will be given later, the light La that has been emitted from the first light source unit 12 is split into the measuring light L1 and the reference light L2 in the optical fiber coupler 14 through the optical fibers FB4 and FB3, and the measuring light L1 is inputted to the optical connector 18.

Further, the second light source unit 13 emits visible light as the aiming light Le in order to make it easier to confirm a measuring site. As the aiming light Le, for example, red semiconductor laser light at a wavelength of 0.66 μm, He—Ne laser light at a wavelength of 0.63 μm, blue semiconductor laser light at a wavelength of 0.405 μm, and so on can be used. Thus, the second light source unit 13, for example, includes a semiconductor laser 13*a* that emits red, blue, or green laser light and a lens 13*b* that converges the aiming light Le emitted from the semiconductor laser 13*a*. The aiming light Le that has been emitted from the second light source unit 13 is inputted to the optical connector 18 through the optical fiber FB8.

In the optical connector 18, the measuring light L1 and the aiming light Le are combined with each other and guided to the rotative side optical fiber FB1 inside the OCT probe 600.

The optical fiber coupler (the splitting and combining unit) 14 is, for example, configured of two-by-two optical fiber couplers, which are optically connected to the fixed side optical fiber FB2, the optical fiber FB3, the optical fiber FB5, and the optical fiber FB7, respectively.

The optical fiber coupler 14 splits the light La that has entered from the first light source unit 12 through the optical fibers FB4 and FB3 into the measuring light (the first light beam) L1 and the reference light L2 and causes the measuring light L1 to enter the fixed side optical fiber FB2 and the reference light L2 to enter the optical fiber FB5.

In addition, the optical fiber coupler 14 combines the light L2 that has entered the optical fiber FB5 and returned through the optical fiber FB5 after being subjected to a frequency shift and to an optical path length modification in the optical path length adjusting unit 26, which will be described later, with the light L3 that has been acquired in the OCT probe 600, which will be described later, and guided through the fixed side optical fiber FB2 and emits to the optical fiber FB3 (FB6) and the optical fiber FB7.

The OCT probe 600 is connected to the fixed side optical fiber FB2 through the optical connector 18, and the measuring light L1 that has been combined with the aiming light Le enters the rotative side optical fiber FB1 from the fixed side optical fiber FB2 through the optical connector 18. This entering measuring light L1 that has been combined with the aiming light Le is transmitted by the rotative side optical fiber FB1 to be applied onto the measuring subject S. Then, the OCT probe 600 acquires the returning light L3 from the measuring subject S and transmits the acquired returning light L3 by the rotative side optical fiber FB1 to emit to the fixed side optical fiber FB2 through the optical connector 18.

The optical connector 18 combines the measuring light (the first light beam) L1 with the aiming light (the second light beam) Le.

The interfered light detecting unit 20 is connected to the optical fiber FB6 and the optical fiber FB7 and detects as the interference signal the interfered lights L4 and L5 that have been generated by combining the reference light L2 with the returning light L3 in the optical fiber coupler 14.

Here, the OCT processor 400 includes the detector 30*a* that is provided on the optical fiber FB6 that is split from the optical fiber coupler 28 and detects an optical intensity of the interfered light L4 and the detector 30*b* that detects an optical intensity of the interfered light L5 in an optical path of the optical fiber FB7.

The interfered light detecting unit 20 generates an interference signal based on detection results of the detector 30*a* and the detector 30*b*.

The signal processing unit 22 acquires a tomographic image from the interference signal that has been detected by the interfered light detecting unit 20 and outputs the acquired tomographic image to the monitor device 500. Note that, in the present embodiment, generation of a tomographic image and generation of a surface image of the measuring subject S are carried out in parallel based on the interference signal that has been detected by the interfered light detecting unit 20, and the tomographic image and the surface image are displayed on the monitor device 500 in real time and at the same time. The detailed configuration of the signal processing unit 22 for achieving the above will be described later.

The optical path length adjusting unit 26 is arranged to an emission side of the reference light L2 from the optical fiber FB5 (that is, at an end portion of the optical fiber FB5 opposite to the optical fiber coupler 14).

The optical path length adjusting unit 26 includes a first optical lens 80 that collimates light emitted from the optical fiber FB5, a second optical lens 82 that converges the light collimated by the first optical lens 80, a reflection mirror 84 that reflects the light converged by the second optical lens 82, a base 86 that supports the second optical lens 82 and the reflection mirror 84, and a mirror moving mechanism 88 that moves the base 86 in a direction parallel to an optical axis direction and varies a distance between the first optical lens 80 and the second optical lens 82 to adjust the optical length of the reference light L2.

The first optical lens 80 collimates the reference light L2 that has been emitted from the core of the optical fiber FB5 and also converges the reference light L2 that has been reflected by the reflection mirror 84 onto the core of the optical fiber FB5.

Further, the second optical lens 82 converges the reference light L2 that has been collimated by the first optical lens 80 onto the reflection mirror 84 and also collimates the reference light L2 that has been reflected by the reflection mirror 84. In this way, a confocal optical system is formed by the first optical lens 80 and the second optical lens 82.

In addition, the reflection mirror 84 is arranged at a focus point of the light to be converged by the second optical lens 82 and reflects the reference light L2 that has been converged by the second optical lens 82.

Through this, the reference light L2 that has been emitted from the optical fiber FB5 is collimated by the first optical lens 80 and converged onto the reflection mirror 84 by the second optical lens 82. Thereafter, the reference light L2 that has been reflected by the reflection mirror 84 is collimated by the second optical lens 82 and converged onto the core of the optical fiber FB5 by the first optical lens 80.

Further, the base 86 fixes the second optical lens 82 and the reflection mirror 84, and the mirror moving mechanism 88 moves the base 86 in the optical axis direction of the first optical lens 80 (a direction of an arrow A in FIG. 2).

By moving the base 86 in the direction of the arrow A through the mirror moving mechanism 88, the distance between the first optical lens 80 and the second optical lens 82 can be modified, and the optical path length of the reference light L2 can be adjusted.

The operation control unit 32 includes an input device such as a keyboard and a mouse and a control device that manages various conditions based on inputted information and is connected to the signal processing unit 22. The operation control unit 32 inputs, sets, and modifies various processing conditions and so on in the signal processing unit 22 based on an instruction of an operator inputted from the input device.

Note that the operation control unit 32 may display an operation screen on the monitor device 500 or may be provided with a separate display unit to display an operation screen. Further, an operation control or a setup of various conditions of the first light source unit 12, the second light source unit 13, the optical connector 18, the interfered light detecting unit 20, the optical path length, and the detectors 30*a* and 30*b* may be carried out through the operation control unit 32.

[OCT Probe]

Figure 3:
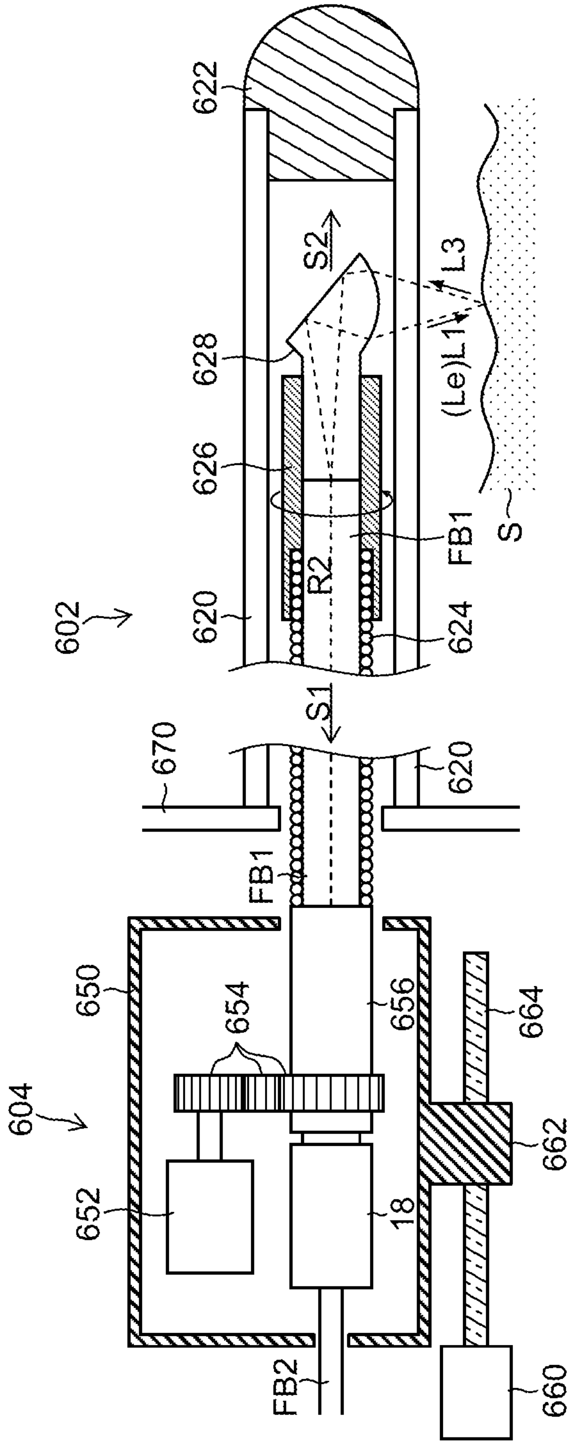
FIG. 3 is a sectional view of an OCT probe of FIG. 2.

FIG. 3 is a sectional view of the OCT probe of FIG. 2.

As illustrated in FIG. 3, the leading end portion of the insertion unit 602 includes a probe external cylinder 620, a cap 622, the rotative side optical fiber FB1, a spring 624, a fixing member 626, and an optical lens 628.

The probe external cylinder (a sheath) 620 is a cylindrical member having flexibility and is formed of a material that transmits the measuring light L1 that has been combined with the aiming light Le in the optical connector 18 and the returning light L3. Note that it is sufficient that, of the probe external cylinder 620, a part of the leading end side (the leading end of the rotative side optical fiber FB1 opposite to the optical connector 18, hereinafter, referred to as the leading end of the probe external cylinder 620) through which the measuring light L1 (the aiming light Le) and the returning light L3 pass is formed of a material (a transparent material) that transmits light along the entire circumference, and portions other than the leading end may be formed of a material that does not transmit light.

The cap 622 is provided at the leading end of the probe external cylinder 620 and closes off the leading end of the probe external cylinder 620.

The rotative side optical fiber FB1 is a linear member and is housed inside the probe external cylinder 620 along the probe external cylinder 620. The rotative side optical fiber FB1 guides, to the optical lens 628, the measuring light L1 that has been emitted from the fixed side optical fiber FB2 and combined with the aiming light Le that has been emitted from the optical fiber FB8 through the optical connector 18. The rotative side optical fiber FB1 guides, to the optical connector 18, the returning light L3 from the measuring subject S acquired through the optical lens 628 by applying the measuring light L1 (the aiming light Le) onto the measuring subject S. The returning light L3 that has been guided to the optical connector 18 enters the fixed side optical fiber FB2.

Here, the rotative side optical fiber FB1 and the fixed side optical fiber FB2 are connected to each other through the optical connector 18 and are optically connected to each other in a state where rotation of the rotative side optical fiber FB1 does not propagate to the fixed side optical fiber FB2. Further, the rotative side optical fiber FB1 is arranged so as to freely rotate with respect to the probe external cylinder 620 and to freely move in an axial direction of the probe external cylinder 620.

The spring 624 is fixed to the periphery of the rotative side optical fiber FB1. Further, the rotative side optical fiber FB1 and the spring 624 are connected to the optical connector 18.

The optical lens 628 is arranged at a measuring side leading end (the leading end of the rotative side optical fiber FB1 opposite to the optical connector 18) of the rotative side optical fiber FB1. The leading end portion of the optical lens 628 is formed into a substantially spherical shape in order to converge the measuring light L1 (the aiming light Le) emitted from the rotative side optical fiber FB1 onto the measuring subject S.

The optical lens 628 radiates the measuring light L1 (the aiming light Le) emitted from the rotative side optical fiber FB1 onto the measuring subject S and converges the returning light L3 from the measuring subject S so as to enter the rotative side optical fiber FB1.

The fixing member 626 is arranged on the periphery of a connection part of the rotative side optical fiber FB1 and the optical lens 628 and fixes the optical lens 628 to an end portion of the rotative side optical fiber FB1. Here, a method of fixing the rotative side optical fiber FB1 with the optical lens 628 through the fixing member 626 is not particularly limited, and the rotative side optical fiber FB1 and the optical lens 628 may be bonded and fixed to the fixing member 626 with an adhesive or may be fixed through a mechanical structure using a bolt or the like. Note that any member such as a zirconia ferrule and a metal ferrule may be used for the fixing member 626 as long as such member is used for fixing, holding, or protecting an optical fiber.

Further, the rotative side optical fiber FB1 and the spring 624 are connected to a rotative cylinder 656, which will be described later, and, by rotating the rotative side optical fiber FB1 and the spring 624 through the rotative cylinder 656, causes the optical lens 628 to rotate in a direction of an arrow R2 with respect to the probe external cylinder 620. Further, the optical connector 18 includes a rotary encoder and detects an application position of the measuring light L1 from positional information (angular information) of the optical lens 628 based on a signal from the rotary encoder. In other words, an angle with respect to a reference position in a rotating direction of the rotating optical lens 628 is detected to detect a measurement position.

In addition, the rotative side optical fiber FB1, the spring 624, the fixing member 626, and the optical lens 628 are configured to be movable through an actuating unit, which will be described later, in a direction of an arrow S1 (a direction toward the forceps opening) and in an S2 direction (a direction toward the leading end of the probe external cylinder 620) inside the probe external cylinder 620.

Further, the left side of FIG. 3 is a diagram that illustrates a schematic of the actuating unit for the rotative side optical fiber FB1 and so on in the operating unit 604 of the OCT probe 600.

The probe external cylinder 620 is fixed to a fixing member 670. In contrast, the rotative side optical fiber FB1 and the spring 624 are connected to the rotative cylinder 656, and the rotative cylinder 656 is configured to rotate through a gear 654 in response to rotation of a motor 652. The rotative cylinder 656 is connected to the optical connector 18, and the measuring light L1 and the returning light L3 are transmitted between the rotative side optical fiber FB1 and the fixed side optical fiber FB2 through the optical connector 18.

Further, a frame 650 that houses the rotative cylinder 656, the motor 652, the gear 654, the optical connector 18, and so on includes a support member 662. The support member 662 has a threaded hole. An advance/retreat moving ball screw 664 engages into the threaded hole. The advance/retreat moving ball screw 664 is connected to a motor 660. Accordingly, rotatively driving the motor 660 causes the frame 650 to move to advance or retreat, and through this the rotative side optical fiber FB1, the spring 624, the fixing member 626, and the optical lens 628 can be moved in the S1 and S2 directions in FIG. 3.

The OCT probe 600 is configured as above, in which as the rotative side optical fiber FB1 and the spring 624 are rotated in the direction of the arrow R2 in FIG. 3 through the optical connector 18, the measuring light L1 (the aiming light Le) that has been emitted from the optical lens 628 is applied onto the measuring subject S while scanning in the direction of the arrow R2 (a circumferential direction of the probe external cylinder 620) and the returning light L3 is acquired. The aiming light Le is applied onto the measuring subject S, for examples, as blue, red, or green spot light. Reflected light of this aiming light Le is displayed as a bright spot in an observation image displayed on the monitor device 500.

Through this, a desired site of the measuring subject S can be accurately captured along the entire periphery in the circumferential direction of the probe external cylinder 620, and the returning light L3 reflected by the measuring subject S can be acquired.

In addition, in a case where a plurality of tomographic images are to be acquired to generate three dimensional volume data, the optical lens 628 is moved through the actuating unit to an end edge of a movable range in the direction of the arrow Si and then moved in the S2 direction in increments of a predetermined amount while acquiring a tomographic image or moved to an end edge of a movable range while alternately repeating acquisition of a tomographic image and movement in the S2 direction by a predetermined amount.

In this way, by obtaining a plurality of pieces of waveform data of the measuring subject S in a desired range, a surface image of the measuring subject S can be obtained, and three dimensional volume data can also be obtained based on the plurality of acquired tomographic images.

Figure 4:
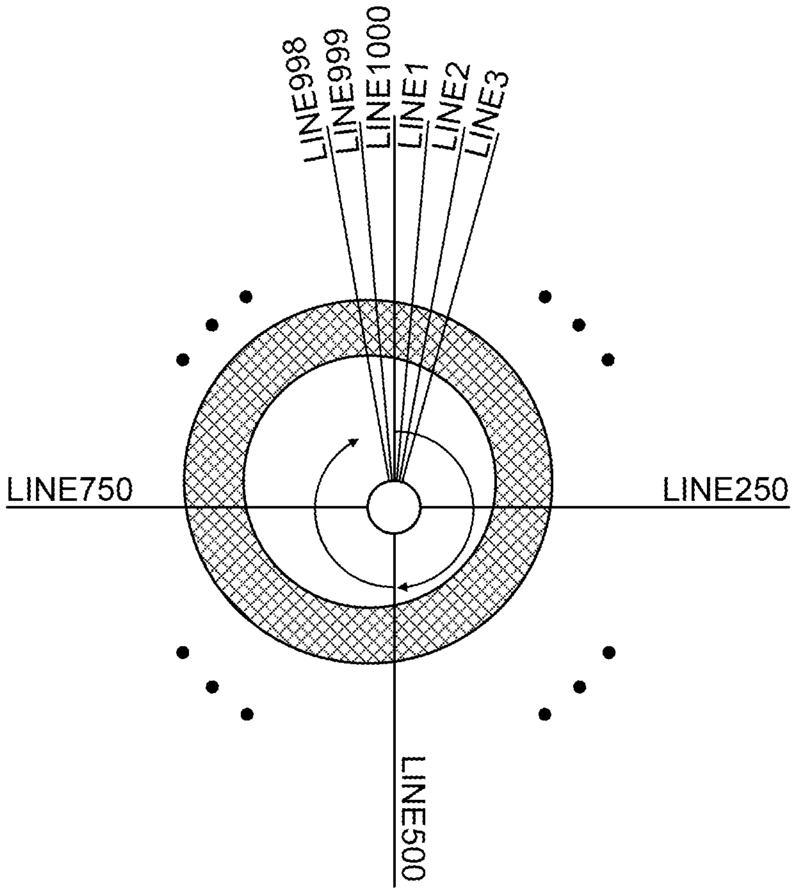
FIG. 4 is a diagram that illustrates a scan plane of a tomographic image in a case where optical scanning is radial scanning with respect to a measuring subject S of FIG. 2.
Figure 5:
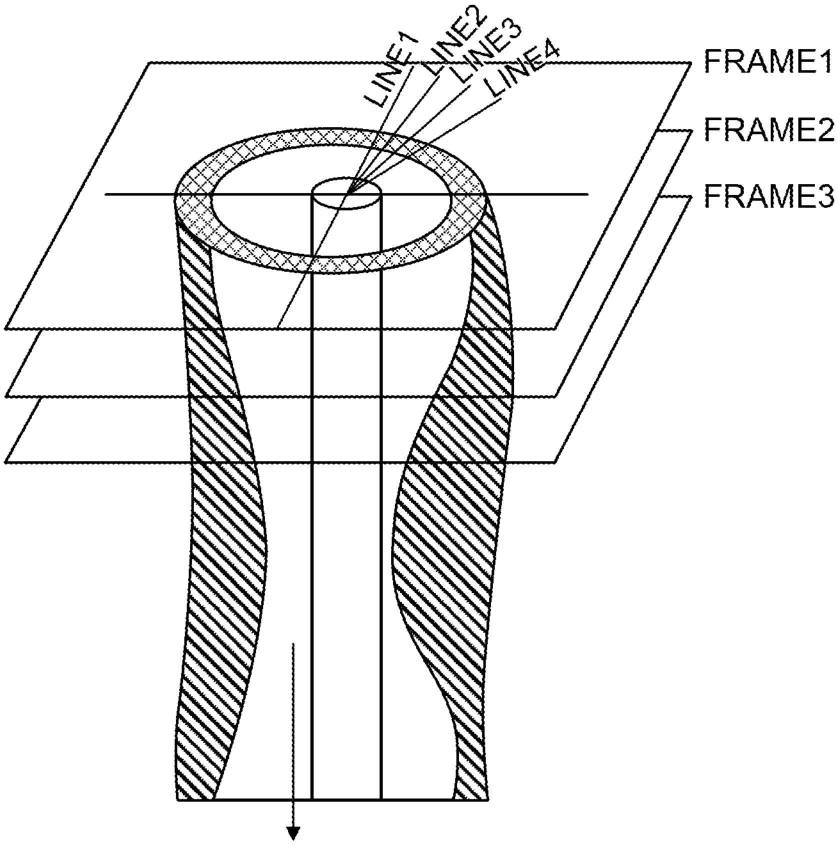
FIG. 5 is a diagram that illustrates three dimensional volume data that are constructed from the tomographic image of FIG. 4.

FIG. 4 is a diagram that illustrates a scan plane of a tomographic image in a case where optical scanning is radial scanning with respect to the measuring subject S of FIG. 2. FIG. 5 is a diagram that illustrates three dimensional volume data to be constructed from the tomographic images of FIG. 4.

A tomographic image of the measuring subject S in a depth direction (a first direction) is acquired through an interference signal, and the measuring subject S is scanned (radially scanned) in the direction of the arrow R2 in FIG. 3 (the circumferential direction of the probe external cylinder 620), through this, as illustrated in FIG. 4, a tomographic image can be acquired along a scan plane that contains the first direction and a second direction that is orthogonal to the first direction. In addition, by moving the scan plane along a third direction that is orthogonal to the scan plane, a plurality of tomographic images can be acquired to generate three dimensional volume data, as illustrated in FIG. 5.

Figure 6:
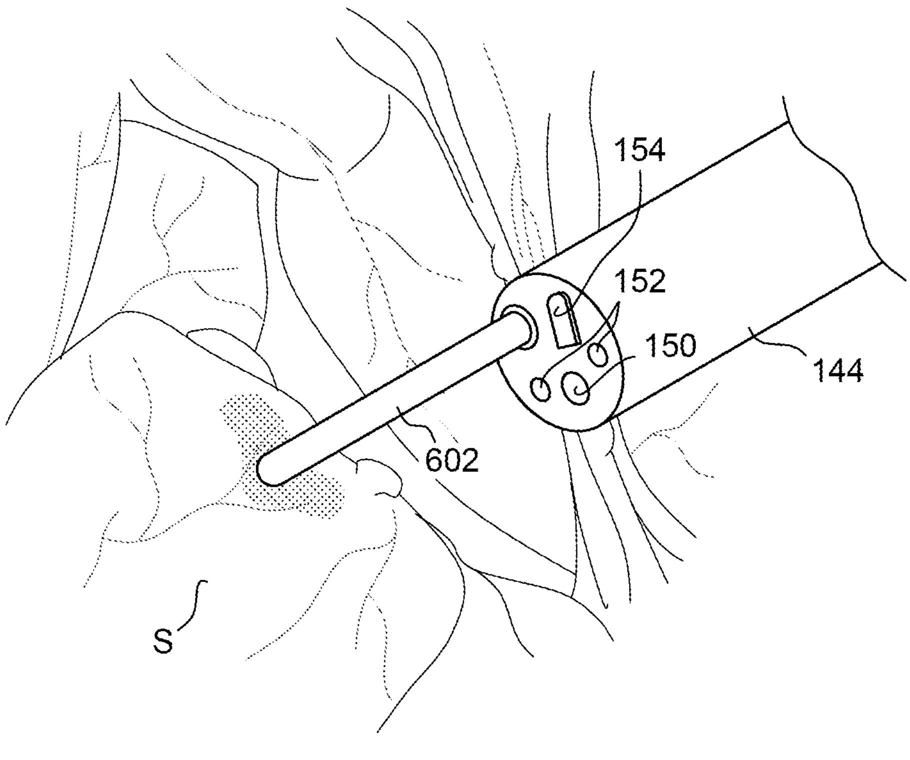
FIG. 6 is a diagram that illustrates a state where a tomographic image is obtained using an OCT probe that has been led out from a forceps opening of an endoscope of FIG. 1.

FIG. 6 is a diagram that illustrates a state where a tomographic image is obtained using an OCT probe that has been led out from the forceps opening of the endoscope of FIG. 1. As illustrated in FIG. 6, a tomographic image is obtained with the leading end portion of the insertion unit 602 of the OCT probe being brought close to a desired site of the measuring subject S. In a case where a plurality of tomographic images of a desired range are to be obtained, the main body of the OCT probe 600 does not need to be moved, but the optical lens 628 may be moved within the probe external cylinder 620 through the above-described actuating unit.

Figure 7:
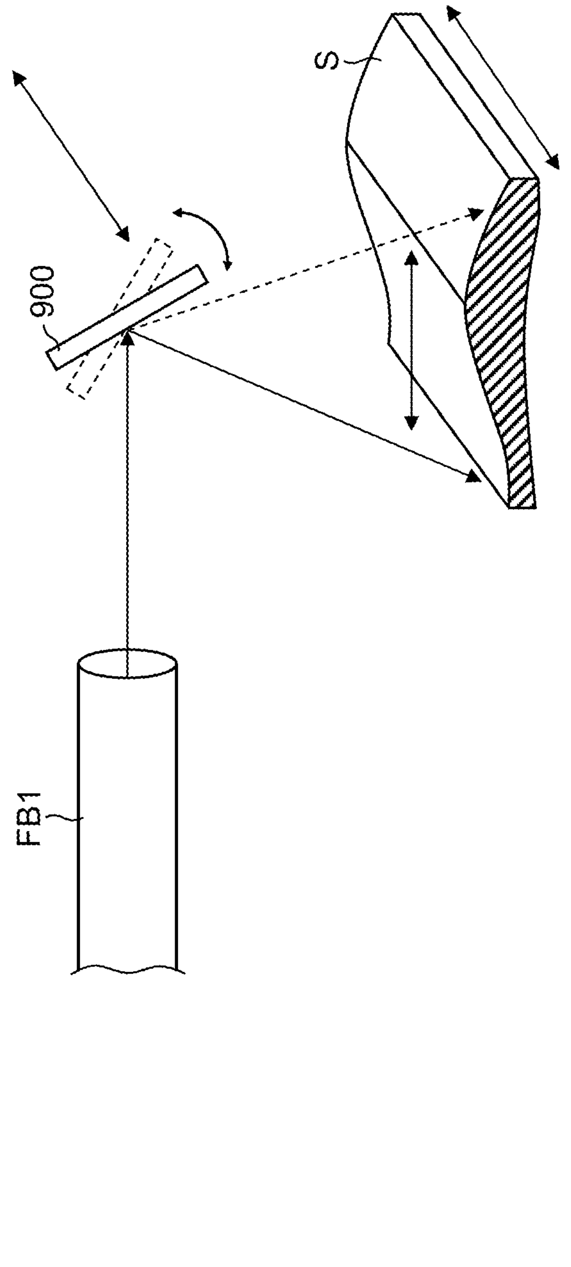
FIG. 7 is a diagram that illustrates a configuration for acquiring a tomographic image by carrying out sector scanning with respect to the measuring subject S of FIG. 2.
Figure 8:
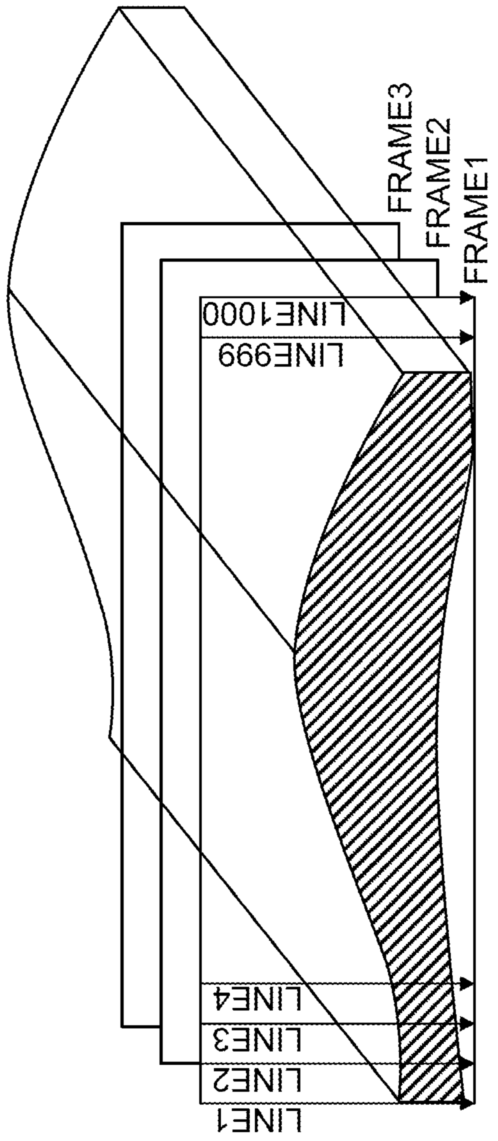
FIG. 8 is a diagram that illustrates three dimensional volume data that are constructed from the tomographic image of FIG. 7.

Note that although the measuring subject S has been radially scanned with the measuring light L1 (the aiming light Le), the configuration is not limited thereto. FIG. 7 is a diagram that illustrates a configuration where a tomographic image is acquired by carrying out sector scanning with respect to the measuring subject S of FIG. 2, and FIG. 8 is a diagram that illustrates three dimensional volume data to be constructed from the tomographic images of FIG. 7. As illustrated in FIG. 7, the present invention can also be applied to a configuration where a galvano-mirror 900 is used and a tomographic image is acquired by carrying out sector scanning from above the measuring subject S. In the example in FIG. 7 as well, by moving the scan plane, a plurality of tomographic images can be acquired to generate the three dimensional volume data as illustrated in FIG. 8.

[Signal Processing Unit]

Figure 9:
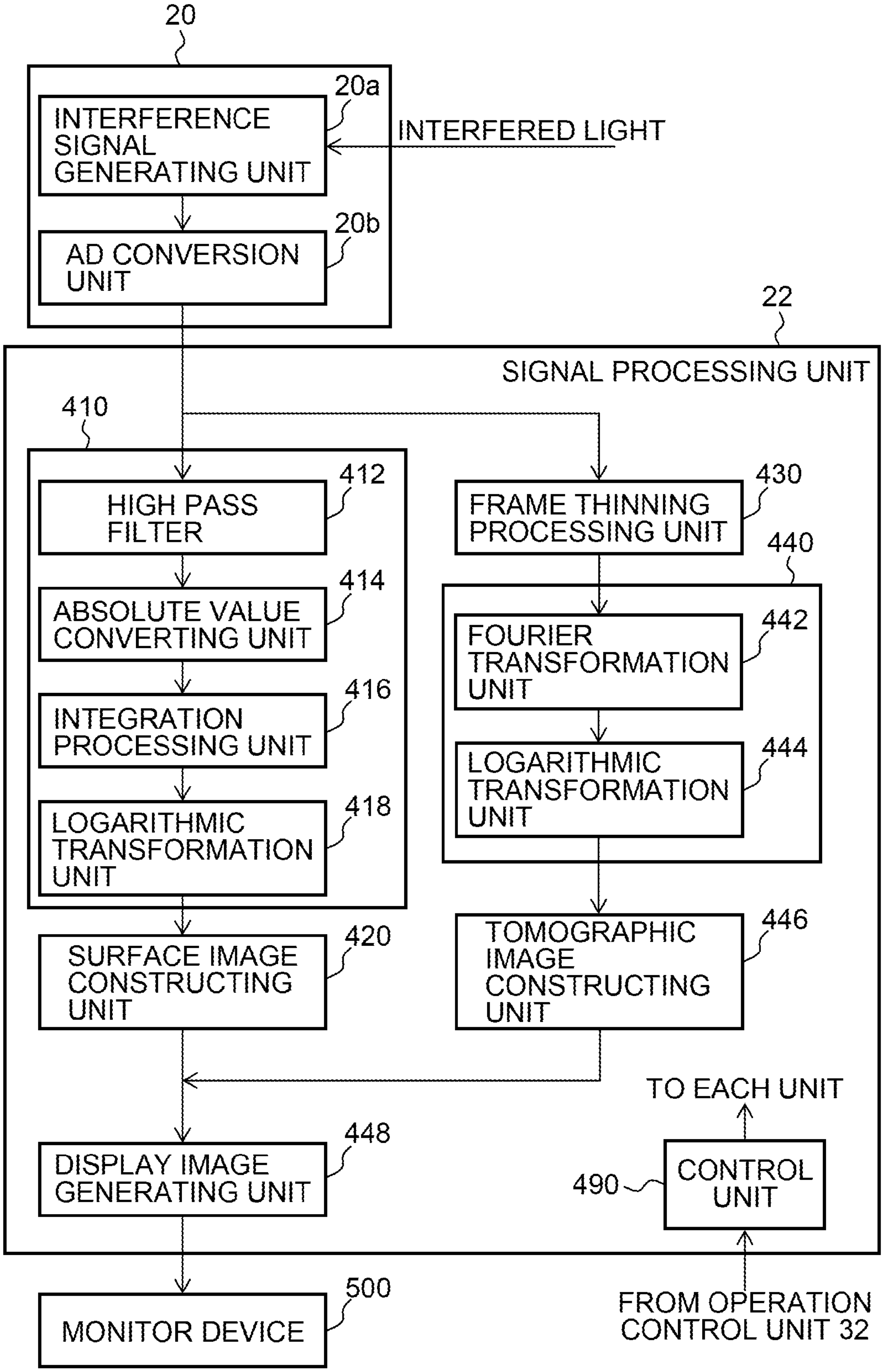
FIG. 9 is a block diagram that illustrates a configuration of a signal processing unit of FIG. 2.

FIG. 9 is a block diagram that illustrates a configuration of the signal processing unit 22 of FIG. 2 and a peripheral portion thereof.

As illustrated in FIG. 9, the interfered light detecting unit 20 includes an interference signal generating unit 20*a* and an AD conversion unit 20*b*. When the interfered light where the returning light L3 from the measuring subject S is combined with the reference light L2 is inputted to the interfered light detecting unit 20, an interference signal (an electrical signal) is generated from the interfered light (an optical signal) by the interference signal generating unit 20*a*. Then, the interference signal that has been generated by the interference signal generating unit 20*a* is converted from an analog signal into a digital signal by the AD conversion unit 20*b* and inputted to the signal processing unit 22.

The signal processing unit 22 of the present embodiment includes a surface data generating unit 410 that generates surface data, a surface image constructing unit 420 that constructs a surface image from the surface data, a frame thinning processing unit 430 that carries out thinning processing of an interference signal on a frame-by-frame basis, a tomographic data generating unit 440 that generates tomographic data, a tomographic image constructing unit 446 that constructs a tomographic image from the tomographic data, a display image generating unit 448 that generates an image to be displayed on the monitor device 500 from the surface image and the tomographic image, and a control unit 490 that controls each unit of the signal processing unit 22 based on an operation signal from the operation control unit 32.

The interference signal that has been inputted to the signal processing unit 22 from the interfered light detecting unit 20 is split into two. One of the split interference signals is inputted to the surface data generating unit 410, and the other interference signal is inputted to the tomographic data generating unit 440 through the frame thinning processing unit 430.

The surface data generating unit 410 includes a high pass filter (HPF) 412, an absolute value converting unit 414, an integration processing unit 416, and a logarithmic transformation unit 418.

The high pass filter 412 removes a low frequency component from the interference signal inputted to the surface data generating unit 410. This is because an interference signal component by the returning light reflected by the probe external cylinder 620 of the OCT probe 600 is at a low frequency side, and, by removing the low frequency component of the interference signal by the high pass filter 412, makes it possible to limit to an interference signal component by the returning light from a living body. A cutoff frequency of the high pass filter 412 is set to be capable of removing a frequency of the interference signal component of an outermost layer of the OCT probe 600 (that is, the probe external cylinder 620).

The absolute value converting unit 414 converts an amplitude value of the interference signal from which the low frequency component has been removed by the high pass filter 412 into an absolute value. Here, a negative component of a waveform of the interference signal is inverted to a positive side, whereby an absolute value conversion is carried out. A method of the absolute value conversion is not limited to that the negative component of the waveform of the interference signal is inverted to the positive side, and the amplitude value of the interference signal may be squared to take a square root thereof, or any generally known methods may be used.

The integration processing unit 416 carries out integration processing on the interference signal that has been converted into an absolute value by the absolute value converting unit 414. Specifically, the entire data for a single line of the interference signal that has been converted into an absolute value, that is, the data for the single line (an interference signal) are entirely integrated in a temporal direction, whereby surface data of the living body in the direction of that line are calculated. Here, although the entire data for the single line are integrated, since the interference signal has been converted from an analog signal to a digital signal by the AD conversion unit 20*b* of the interfered light detecting unit 20 to be turned into discrete data, even when the entire data for the single line are added up, the same result is obtained. In this way, by integrating the data for a single line of an ordinary tomographic image (an OCT image) without carrying out FFT (fast Fourier transformation), a single piece of surface data in the direction of that line is generated. In addition, a single line of a surface image is generated from data for a single frame.

The logarithmic transformation unit 418 carries out logarithmic transformation of the surface data that have been obtained through the integration processing by the integration processing unit 416. The surface data that have been logarithmically transformed are inputted to the surface image constructing unit 420.

The surface image constructing unit 420 constructs a surface image in accordance with the monitor device 500 and a display method thereof based on the surface data generated by the surface data generating unit 410 (that is, the surface data that have been logarithmically transformed in the logarithmic transformation unit 418). Specifically, the surface image is constructed through re-sampling in accordance with brilliance, contrast control, and a display size, through coordinate transformation in accordance with a scanning method, and so on. The surface image that has been constructed in this way is inputted to the display image generating unit 448, which will be described later.

The frame thinning processing unit 430 carries out thinning processing on a frame-by-frame basis on the interference signal inputted from the interfered light detecting unit 20 and outputs an interference signal after the thinning processing to the tomographic data generating unit 440 in a subsequent stage. Specifically, the thinning processing is carried out on a frame-by-frame basis so that the interference signal is outputted at a frame rate equal to or less than that of the monitor device 500.

This is because the radial scanning in OCT is, for example, carried out at a frequency of 100 Hz, and thus an interference signal can be acquired at a frame rate of 100 fps. In contrast, since the frame rate of the monitor device 500 is typically around 30 fps, even if all the interference signals detected by the interfered light detecting unit 20 are processed, not all of the frames can be displayed. Therefore, by subjecting the interference signal to the thinning processing on a frame-by-frame basis at this stage, time that can be spared for later stage processing can be increased. Further, in fact, diagnosis is sufficiently possible even when the frame rate of the monitor device 500 is around 15 fps, and thus by carrying out the thinning processing on the interference signal in a range where diagnosis is possible, a load on later processing can be reduced.

In the present embodiment, a mode in which the frame rate of the interference signal to be outputted from the frame thinning processing unit 430 is automatically varied in accordance with the frame rate of the monitor device 500 is preferable. For example, a reading device is provided to read the frame rate of the monitor device 500, and the interference signal is made to be outputted from the frame thinning processing unit 430 at a frame rate equal to or less than the frame rate read by the reading device.

Further, a mode in which the frame rate of the interference signal to be outputted from the frame thinning processing unit 430 can be manually varied is also preferable. For example, when an operator specifies a frame rate or a thinning rate through the operation control unit 32, the frame thinning processing unit 430 carries out the thinning processing on the interference on a frame-by-frame basis in accordance with the specified frame rate or thinning rate. According to this mode, the frame rate of the interference signal to be inputted to the tomographic data generating unit 440 can be varied in accordance with the operator's intension or preference, and thus a processing load of the signal processing unit 22 can be further reduced.

The tomographic data generating unit 440 is a processing unit that generates the tomographic data based on the interference signal inputted from the interfered light detecting unit 20 through the frame thinning processing unit 430 and is configured of a Fourier transformation unit 442 and a logarithmic transformation unit 444.

The Fourier transformation unit 442 frequency-resolves the interference signal that has been subjected to the thinning processing by the frame thinning processing unit 430 through FFT (fast Fourier transformation) to generate an intensity of the returning light L3 at each depth position of the measuring subject S, that is, reflection intensity data (tomographic data) for a single line in the depth direction.

The logarithmic transformation unit 444 carries out logarithmic transformation of the tomographic data that have been Fourier-transformed in the Fourier transformation unit 442. The tomographic data that have been logarithmically transformed are inputted to the tomographic image constructing unit 446.

The tomographic image constructing unit 446 constructs a tomographic image in accordance with the monitor device 500 and a display method thereof from the tomographic data that have been generated by the tomographic data generating unit 440 (that is, the tomographic data that have been logarithmically transformed in the logarithmic transformation unit 444). Specifically, the tomographic image is constructed through re-sampling in accordance with brilliance, contrast control, and a display size, through coordinate transformation in accordance with a scanning method such as radial scanning and sector scanning, and so on. The tomographic image that has been constructed in this way is inputted to the display image generating unit 448, which will be described later.

The display image generating unit 448 generates an image to be displayed on the monitor device 500 from the surface image that has been constructed by the surface image constructing unit 420 and the tomographic image that has been constructed by the tomographic image constructing unit 446 and outputs that image to the monitor device 500.

Subsequently, an action of the present embodiment configured as described above will be described.

First, of the interference signals that have been inputted from the interfered light detecting unit 20 to the signal processing unit 22 and that have been split into two, one of the interference signals is inputted to the surface data generating unit 410, and generation processing of the surface data is carried out.

As for specific processing to be carried out by the surface data generating unit 410, first, a low frequency component is removed from the interference signal by the high pass filter 412. Through this, an interference signal component by the returning light reflected by the probe external cylinder 620 is removed to limit to an interference signal component by the returning light reflected by the living body. Subsequently, after the amplitude value of the interference signal is converted into an absolute value by the absolute value converting unit 414, the entire data for a single line, that is, the data for the single line (interference signal) are entirely integrated in a temporal direction by the integration processing unit 416. Through this, the surface data of the living body in the direction of that line are calculated. In addition, the surface data are logarithmically transformed in the logarithmic transformation unit 418.

The surface data that have been generated by the surface data generating unit 410 in this way are inputted to the surface image constructing unit 420. In the surface image constructing unit 420, once the surface data for the single line (or a single frame) are accumulated, a surface image is generated based on the accumulated surface data.

On the other hand, of the interference signals that have been inputted from the interfered light detecting unit 20 to the signal processing unit 22 and that have been split into two, the other interference signal is inputted to the tomographic data generating unit 440 through the frame thinning processing unit 430.

The interference signal that has been inputted to the frame thinning processing unit 430 is subjected to the thinning processing on a frame-by-frame basis. Specifically, the thinning processing is carried out so that the interference signal is outputted at a frame rate equal to or less than the frame rate of the monitor device 500. The interference signal after the thinning processing is inputted to the tomographic data generating unit 440, and generation processing of the tomographic data is carried out.

As for specific processing to be carried out in the tomographic data generating unit 440, first, when the interference signal that has been subjected to the thinning processing by the frame thinning processing unit 430 is inputted, a frequency analysis through FFT (fast Fourier transformation) is carried out by the Fourier transformation unit 442. Through this, reflection intensity data (tomographic data) in the depth direction of the measuring subject S are generated. Subsequently, the tomographic data that have been generated by the Fourier transformation unit 442 are logarithmically transformed in the logarithmic transformation unit 444.

The tomographic data that have been generated by the tomographic data generating unit 440 in this way are inputted to the tomographic image constructing unit 446. In the tomographic image constructing unit 446, once the tomographic data for a single frame are accumulated, a tomographic image is generated based on the accumulated tomographic data.

In the display image generating unit 448, a display image is generated from the surface image that has been constructed by the surface image constructing unit 420 and the tomographic image that has been constructed by the tomographic image constructing unit 446. The display image that has been generated in this way is outputted to the monitor device 500.

Figure 10:
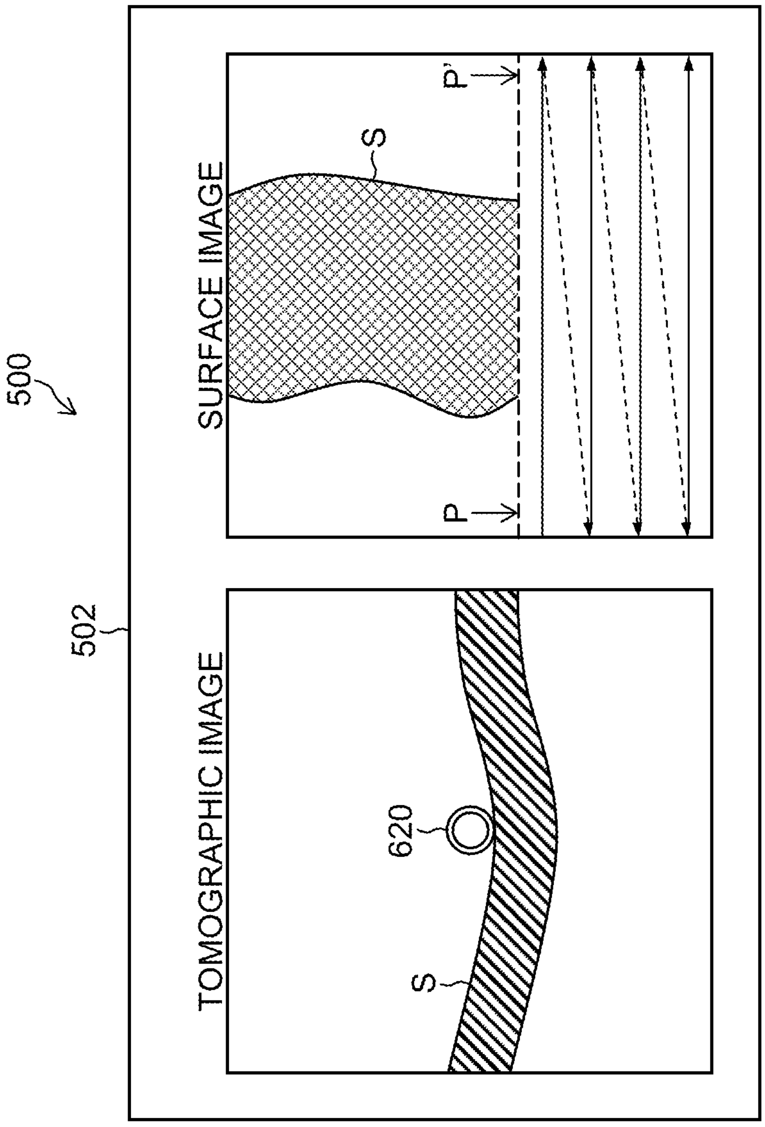
FIG. 10 is a diagram that illustrates an example of an image displayed on a monitor device.

Here, an example of an image to be displayed on the monitor device 500 is illustrated in FIG. 10. As illustrated in FIG. 10, the surface image and the tomographic image are displayed side by side on a display screen 502 of the monitor device 500. Note that the tomographic image that is illustrated in the left side of the display screen 502 illustrates a tomographic image at a section along P-P' line of the surface image on the right side.

In the example illustrated in FIG. 10, the tomographic image is updated each time tomographic data for a single frame are generated, whereas the surface image is updated each time surface data for a single line (or a single frame) are generated. For example, when the surface data for a single line are generated, a surface image of a single point corresponding to that position is added. Then, in accordance with the scanning of the OCT probe 600, surface images are successively added from left to right and from top to bottom in FIG. 10. At this time, the tomographic image is updated each time tomographic data for a single frame are generated. Note that surface images for a single frame (that is, a single horizontal line of the surface image of FIG. 10) may collectively be added each time surface data for a single frame are generated.

In this way, according to the present embodiment, generation of the tomographic data and generation of the surface data are carried out in parallel from the interference signal acquired by scanning with the OCT probe 600, which makes it possible to display the tomographic image and the surface image on the monitor device 500 in real time and at the same time without reconstructing the surface image from the three dimensional volume data. This makes it possible for an operator to observe not only a tomographic image of a lesion portion but also a surface image at the same time, which facilitates a selection of a method of treatment.

[Second Embodiment]

Subsequently, a second embodiment of the present invention will be described. Hereinafter, descriptions of parts that are common to those of the first embodiment are omitted, and the description will center on parts that are characteristic to the present embodiment.

In the first embodiment, the interference signal that has been inputted from the interfered light detecting unit 20 is split into two, and a surface image is generated from one of the interference signals. The other interference signal is subjected to the thinning processing on a frame-by-frame basis, and then a tomographic image is generated threrefrom. A reason for configuring as such is to facilitate generation of the tomographic image by thinning the interference signal at an interval suitable for the frame rate of the monitor device 500. At this time, in the generation processing of the surface data, the surface data can be generated without carrying out FFT (fast Fourier transformation) that involves complex processing.

In contrast, the second embodiment is a mode in which the thinning processing of the interference signal is omitted and is a mode that is suitable in a case where the frame rate of the interference signal acquired through the scanning by the OCT probe 600 (that is, the frame rate of the interference signal inputted from the interfered light detecting unit 20) is approximately at the same level as the frame rate of the monitor device 500.

Figure 11:
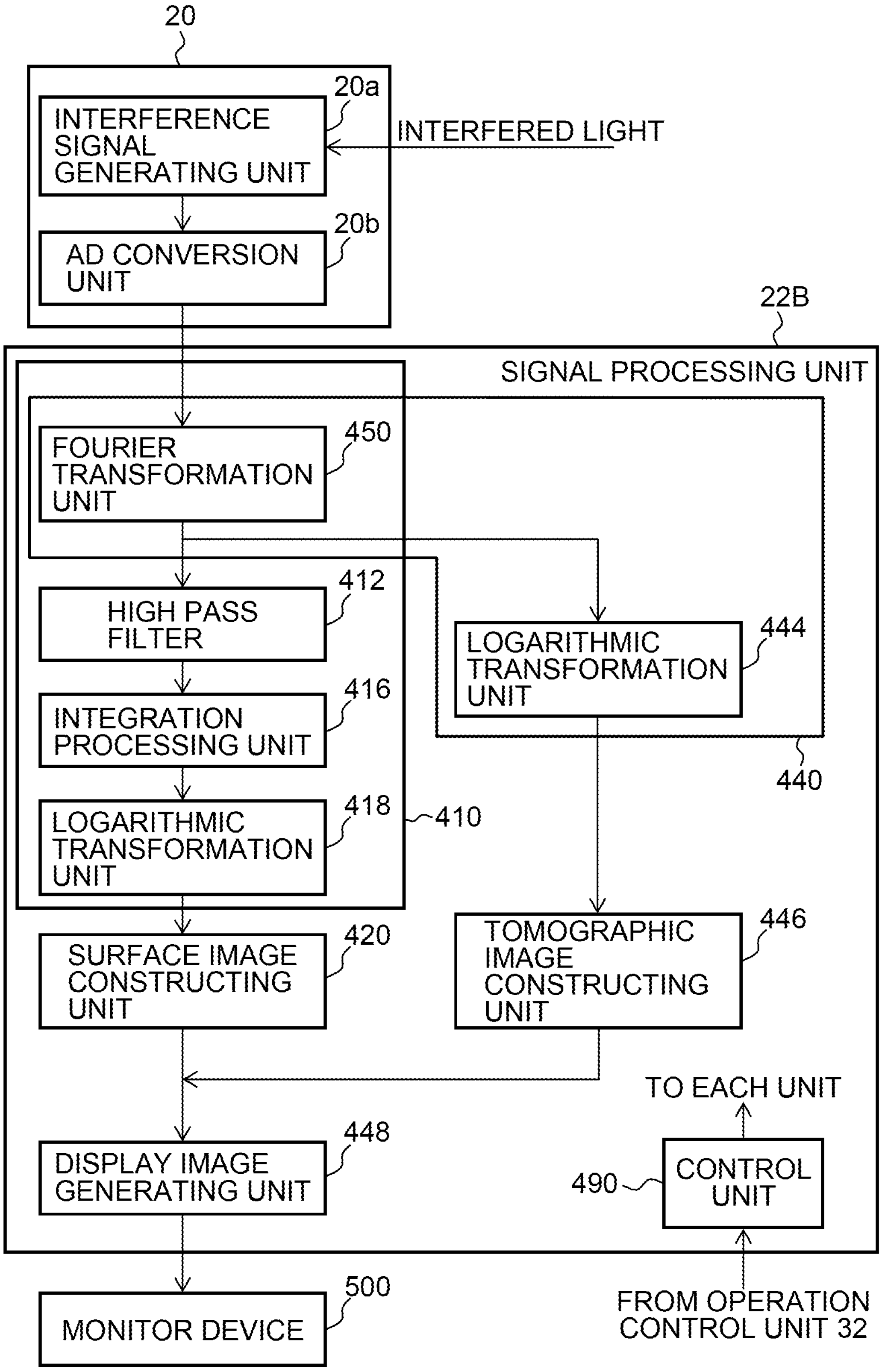
FIG. 11 is a block diagram that illustrates a configuration of a signal processing unit according to a second embodiment.

FIG. 11 is a block diagram that illustrates a configuration of a signal processing unit according to the second embodiment. In FIG. 11, elements that are common or similar to those in FIG. 9 are given the same numerals.

As illustrated in FIG. 11, a signal processing unit 22B in the second embodiment does not include the frame thinning processing unit 430 of the first embodiment (see FIG. 9), and the interference signal that has been outputted from the interfered light detecting unit 20 is inputted to a Fourier transformation unit 450.

The Fourier transformation unit 450 is a common processing unit for the surface data generating unit 410 and the tomographic data generating unit 440 and frequency resolves the inputted interference signal through FFT (fast Fourier transformation) to generate an intensity of the returning light L3 at each depth position of the measuring subject S, that is, reflection intensity data (tomographic data) for a single line in the depth direction. Note that it is needless to say that the Fourier transformation unit 450 may be provided separately in the surface data generating unit 410 and the tomographic data generating unit 440.

The tomographic data outputted from the Fourier transformation unit 450 are split into two, and a low frequency component is removed from one piece of the tomographic data by the high pass filter 412. Through this, an interference signal component by the returning light reflected by the probe external cylinder 620 is removed to limit to a signal component by the returning light reflected by the living body. In addition, the entire data for a single line are integrated by the integration processing unit 416 (in other words, the data that have been Fourier-transformed are entirely integrated in a frequency axis direction), and surface data for a single point corresponding to that line are outputted. Although integration is used here, since the data are turned into discrete data through AD conversion, the same result can be obtained even by adding the entire data for the single line. The data that have been outputted from the integration processing unit 416 are logarithmically transformed in the logarithmic transformation unit 418. The logarithmically transformed data are inputted to the surface image constructing unit 420. On the other hand, the other piece of the tomographic data outputted from the Fourier transformation unit 450 is logarithmically transformed in the logarithmic transformation unit 444 and then inputted to the tomographic image constructing unit 446. Processing from this point forward is the same as that of the first embodiment.

According to the second embodiment, the interference signal that has been inputted to the signal processing unit 22B from the interfered light detecting unit 20 is not subjected to the thinning processing, and generation processing of the tomographic image and generation processing of the surface image are carried out in parallel. Accordingly, the second embodiment is a mode that is suitable in a case where the frame rate of the interference signal acquired through the scanning by the OCT probe 600 (that is, the frame rate of the interference signal inputted from the interfered light detecting unit 20) is approximately at the same level as the frame rate of the monitor device 500, and the thinning processing of the interference signal can be omitted, which allows the signal processing unit 22B to be configured simply.

Note that in each of the embodiments described above, the description has been given sing the SS-OCT (Swept Source OCT) apparatus as the OCT processor 400, but without being limited thereto, the description is applicable even when the OCT processor 400 is the SD-OCT (Spectral Domain OCT) apparatus.

Thus far, the optical tomographic imaging system and the optical tomographic imaging method of the present invention have been described in detail, but the present invention is not limited to the above-described examples, and it is needles to say that various improvements and modifications may be made within a scope that does not depart from the spirit of the present invention.

REFERENCE SIGNS LIST

10 . . . diagnostic imaging apparatus, 20 . . . interfered light detecting unit, 20*a* . . . interference signal generating unit, 20*b* . . . AD conversion unit, 22 . . . signal processing unit, 100 . . . endoscope, 200 . . . endoscope processor, 300 . . . light source device, 400 . . . OCT processor, 410 . . . surface data generating unit, 412 . . . high pass filter, 414 . . . absolute value converting unit, 416 . . . integration processing unit, 418 . . . logarithmic transformation unit, 420 . . . surface image constructing unit, 430 . . . frame thinning processing unit, 440 . . . tomographic data generating unit, 442 . . . Fourier transformation unit, 444 . . . logarithmic transformation unit, 446 . . . tomographic image constructing unit, 448 . . . display image generating unit, 450 . . . Fourier transformation unit, 490 . . . control unit, 500 . . . monitor device

The invention claimed is:

1. An optical tomographic imaging system configured to split light emitted from a wavelength sweep light source into measuring light and reference light, configured to radiate the measuring light onto a measuring subject, configured to combine reflection light from the measuring subject with the reference light, configured to detect interfered light obtained by combining the reflection light with the reference light as an interference signal, and configured to Fourier-transform the interference signal to acquire a tomographic image of the measuring subject, the optical tomographic imaging system comprising:

a tomographic data generating unit configured to generate tomographic data of the measuring subject based on the interference signal;

a surface data generating unit configured to carry out processing in parallel with the tomographic data generating unit and configured to generate surface data of the measuring subject based on the interference signal;

a tomographic image constructing unit configured to construct a tomographic image that is based on the tomographic data generated by the tomographic data generating unit;

a surface image constructing unit configured to construct a surface image that is based on the surface data generated by the surface data generating unit;

a display image generating unit configured to generate a display image from the tomographic image and the surface image; and a frame thinning unit configured to carry out thinning processing on the interference signal on a frame-by-frame basis so that the interference signal is outputted at a frame rate equal to or less than a frame rate of a monitor device on which the tomographic image and the surface image are displayed, wherein the interference signal subjected to the thinning processing by the frame thinning unit is inputted to the tomographic data generating unit.

2. The optical tomographic imaging system according to claim 1, wherein the surface data generating unit includes:

an absolute value converting unit configured to output absolute value data in which an amplitude value of the interference signal is converted into an absolute value; and an interference waveform data integrating unit configured to entirely integrate the absolute value data in a temporal direction.

3. The optical tomographic imaging system according to claim 2, wherein the surface data generating unit further includes a logarithmic transformation unit configured to logarithmically transform data that have been entirely integrated by the interference waveform data integrating unit.

4. The optical tomographic imaging system according to claim 2, wherein the surface data generating unit further includes a high pass filter configured to remove a low frequency component from the interference signal, and the surface data generating unit inputs an interference signal from which a low frequency component has been removed by the high pass filter to the absolute value converting unit.

5. The optical tomographic imaging system according to claim 1, wherein the display image generating unit generates an image in which the tomographic image and the surface image are arranged side by side.

6. An optical tomographic imaging method of: splitting light emitted from a wavelength sweep light source into measuring light and reference light; radiating the measuring light onto a measuring subject; combining reflection light from the measuring subject with the reference light; detecting interfered light obtained by combining the reflection light with the reference light as an interference signal; and Fourier-transforming the interference signal to acquire a tomographic image of the measuring subject, the optical tomographic imaging method comprising:

a tomographic data generating step of generating tomographic data of the measuring subject based on the interference signal;

a surface data generating step of carrying out processing in parallel with the tomographic data generating step and generating surface data of the measuring subject based on the interference signal;

a tomographic image constructing step of constructing a tomographic image that is based on the tomographic data generated in the tomographic data generating step;

a surface image constructing step of constructing a surface image that is based on the surface data outputted in the surface data generating step;

a display image generating step of generating a display image from the tomographic image and the surface image; and a frame thinning step of carrying out thinning processing on the interference signal on a frame-by-frame basis so that the interference signal is outputted at a frame rate equal to or less than a frame rate of a monitor device on which the tomographic image and the surface image are displayed, wherein the interference signal subjected to the thinning processing by the frame thinning unit is inputted to the tomographic data generating unit.

7. The optical tomographic imaging method according to claim 6, wherein the surface data generating step includes:

an absolute value converting step of outputting absolute value data in which an amplitude value of the interference signal is converted into an absolute value; and an interference waveform data integrating step of entirely integrating the absolute value data in a temporal direction.

8. The optical tomographic imaging method according to claim 7, wherein the surface data generating step further includes a logarithmic transformation step of logarithmically transforming data that have been entirely integrated in the interference waveform data integrating step.

9. The optical tomographic imaging method according to claim 7, wherein the surface data generating step includes a step of removing a low frequency component from the interference signal with a high pass filter; and an interference signal from which a low frequency component has been removed in the step is used in the absolute value converting step.

10. The optical tomographic imaging method according to claim 6, wherein in the display image generating step, an image in which the tomographic image and the surface image are arranged side by side are generated.

* * * * *

UNITED STATES PATENT AND TRADEMARK OFFICE

CERTIFICATE OF CORRECTION

PATENT NO. : 9,140,538 B2
APPLICATION NO. : 13/813380
DATED : September 22, 2015
INVENTOR(S) : Kazuhiro Hirota It is certified that error appears in the above-identified patent and that said Letters Patent is hereby corrected as shown below:

In the specification, column 12, line 2, please replace “Si” with -- S1 --

Signed and Sealed this
Fifteenth Day of March, 2016

Michelle K. Lee
*Director of the United States Patent and Trademark Office*